United States Patent [19]

Fogel

[11] Patent Number: 5,952,389
[45] Date of Patent: Sep. 14, 1999

[54] METHODS OF TREATING TARDIVE DYSKINESIA AND OTHER MOVEMENT DISORDERS

[75] Inventor: Barry S. Fogel, Providence, R.I.

[73] Assignee: Synchroneuron, Waban, Mass.

[21] Appl. No.: 09/006,641

[22] Filed: Jan. 13, 1998

[51] Int. Cl.⁶ ..................................................... A61K 31/13
[52] U.S. Cl. ............................................................. 514/665
[58] Field of Search ............................................. 514/665

[56] References Cited

U.S. PATENT DOCUMENTS

| | | |
|---|---|---|
| 4,122,193 | 10/1978 | Scherm et al. . |
| 4,233,229 | 11/1980 | Chakrabarti . |
| 4,355,043 | 10/1982 | Durlach . |
| 5,061,703 | 10/1991 | Bormann et al. . |
| 5,262,162 | 11/1993 | Bormann et al. . |
| 5,382,601 | 1/1995 | Nürnberg et al. . |
| 5,455,279 | 10/1995 | Lipton . |
| 5,614,560 | 3/1997 | Lipton . |

OTHER PUBLICATIONS

Andrew, "Clinical Relationship of Extrapyramidal Symptoms and Tardive Dyskinesia", Can. J. Psych., 39:576–580, 1994.

Bezchilbynk–Butler et al., "Antiparkinsonian Drugs in the Treatment of Neuroleptic–Induced Extrapyramidal Symptoms", Can. J. Psych., 39:74–84, 1994.

Boumans et al., "Is the Social Acceptability of Psychiatric Patients Decreased by Orofacial Dyskinesia?", Schizo Bull, 20:339–344, 1994.

Buchel et al., "Oral Tardive Dyskinesia: Validation of a Measuring Device Using Digital Image Processing", Psychopharmacology—Berl, 117:162–165, 1995.

Chakos et al., "Incidence and Correlates of Tardive Dyskinesia in First Episode of Schizophrenia", Arch Gen Psychiatry, 53:313–319, 1996.

Deckes et al., "Amantadine Hydrochloride Treatment of Tardive Dyskinesia", Oct. 7, New England J. Med, 285:860, 1971.

Delfs et al., "Expression of Glutamic Acid Decarboxylase mRNA in Striatum and Pallidum in an Animal Model of Tardive Dyskinesia", Exp. Neurol, 133:175–188, 1995.

Dimpfel, "Effects of Memantine on Synaptic Transmission in the Hippocampus in Vitro", Arzneimittelforschung, 45:1–5, 1995.

Erdo et al., "Memantine is Highly Potent in Protecting Cortical Cultures against Excitotoxic Cell Death Evoked by Glutamate and N–Methyl–D–Aspartate", Eur. J. Pharmacol, 198:215–217, 1991.

Gao et al., "Taigabine Inhibits Haloperidol–Induced Oral Dyskinesias in Rats", J. Neural Transmission, 95:63–69, 1994.

Hayashi et al., "Prevalence of and Risk Factors for Respiratory Dyskinesia", Clin. Neuropharmacol, 19:390–395, 1996.

Imamura et al., "Improved Preseveration with Amantadine", Abstract, No–To–Shinkei, 46:556–562, 1994.

Jeste et al., "Risk of Tardive Dyskinesia in Older Patients. A Prospective Longitudinal Study of 266 Outpatients", Arch Gen Psychiatry, 52:756–765, 1995.

Keilhoff et al., "Memantine Prevents Quinolinic Acid–Induced Hippocampal Damage", Eur. J. Pharmacol, 219:451–454, 1992.

Kornhuber et al., "New Therapeutic Possibilities with Low–Affinity NMDA Receptor Antagonists", Abstract, Nervenarzt, 67:77–82, 1996.

Lam et al., Vitamin E in the Treatment of Tardive Dyskinesia: A Replication Study, J. Ner. Ment Dis, 182:113–114, 1994.

Latimer, "Tardive Dyskinesia: A Review", Abstract, Can J. Psych, 40:S49–54, 1995.

Lohr et al., "A Double–Blind Placebo–Controlled Study of Vitamin E Treatment of Tardive Dyskinesia", J. Clin. Psychiatry, 57:167–173, 1996.

Muller et al., "Noncompetitive NMDA Receptor Antagonists with Fast Open–Channel Blocking Kinetics and Strong Voltage–Dependency as Potential Therapeutic Agents for Alzheimer's Dementia", Pharmacopsychiatry, 28:113–124, 1995.

Pahl et al., "Positron–Emission Tomography in Tardive Dyskinesia", J. Neuropsych Clin. Neurosci, 7:457–465, 1995.

Raja, "The Treatment of Tardive Dyskinesia", Abstract, Schweiz Arch Neurol Psychaitr, 47:13–18, 1996.

Sachdev et al., "Negative Symptoms, Cognitive Dysfunction, Tardive Akathisia and Tardive Dyskinesia", Acta Psychiatr Scand, 93:451–459, 1996.

Sano et al., "A Controlled Trial of Selegiline, Alpha–Tocopherol, or Both as Treatment for Alzheimer's Disease", The New England Journal of Medicine, vol. 336, No. 17, pp. 1216–1247, Apr. 24, 1997.

Schultz et al., "Neuroprotective Strategies for Treatment of Lesions Produced by Mitochondrial Toxins: Implications for Neurodegenerative Diseases", Neuroscience, 71:1043–1048, 1996.

Silver et al., "No Difference in the Effect of Biperiden and Amatadine on Parkinsonian– and Tardive Dyskinesia–type Involuntary Movements: A Double–Blind Crossover, Placebo–Controlled Study in Medicated Chronic Schizophrenic Patients", Abstract, J. Clin. Psychiatry, 56:167–170, 1995.

Stoessl, "Effects of Ethanol in a Putative Rodent Model of Tardive Dyskinesia", Pharmacol Biochem Behav, 54:541–546, 1996.

Swartz, "Tardive Psychopathology", Neuropsychobiology, 43:115–119, 1995.

(List continued on next page.)

Primary Examiner—Keith D. MacMillan
Attorney, Agent, or Firm—Choate, Hall & Stewart

[57] ABSTRACT

Disclosed is a method for treating a hyperkinetic movement disorder comprising the steps of selecting a first at least one pharmacologically active agent that acts as a GABA-receptor agonist and a second at least one pharmacologically active agent that acts as a NMDA-type glutamate receptor antagonist, and administering the first and second agents at effective and non-toxic dosages.

16 Claims, No Drawings

OTHER PUBLICATIONS

Tirelli et al., "Differential Effects of Direct and Indirect Dopamine Agonists on the Induction of Gnawing in C57B1/6J Mice", J. Pharmacol Exp. Ther., 273:7–15, 1995.

Vale et al., "Amantadine ofr Dyskinesia Tarda", New Eng. J. Med., 284:673, 1971.

Van–Rekum et al., "N of 1 Study: Amantadine for the Amotivational Syndrome in a Patient with Traumatic Brain Injury", Brian Inj. 9:49–53, 1995.

Waddington et al., "Cognitive Dysfunction in Chronic Schizophrenia Followed Prospectively Over 10 Years and Its Longitudinal Relationship to the Emergence of Tardive Dyskinesia", Psychol Med, 26:681–688, 1996.

Wenk et al., "MK–801, Memantine and Amantadine Show Neuroprotective Activity in the Nucleus Baslis Magnocellularis", Eur. J. Pharmacol, 293:267–270, 1995.

Database Chemical Abstracts on STN, 1979:483912, Pycock et al, "Dopamine–dependent hyperactivity in the rat following manipulation of GABA mechanisms in the region of the nucleus accumbens", J. Neural Transm. Jan. 1979, 45(1), 17–33.

METHODS OF TREATING TARDIVE DYSKINESIA AND OTHER MOVEMENT DISORDERS

BACKGROUND OF THE INVENTION

Tardive dyskinesia (TD) is a chronic disorder of the nervous system, characterized by involuntary, irregularly rhythmic movements of the mouth, tongue, and facial muscles. The upper extremities also may be involved. These movements may be accompanied, to a variable extent, by other involuntary movements and movement disorders. These include rocking, writhing, or twisting movements of the trunk (tardive dystonia), forcible eye closure (blepharospasm), an irresistible impulse to move continually (tardive akathisia), jerking movements of the neck, and disrupted respiratory movements (respiratory dyskinesia). The vast majority of cases of TD are caused by the prolonged use of antipsychotic drugs (neuroleptics). (A relatively small number are caused by the use of other medications, such as metoclopramide, that block dopamine receptors.) TD can manifest, or worsen in severity, after neuroleptic drug therapy is discontinued.

The cumulative incidence of TD in patients exhibiting a first episode of schizophrenia who have undergone a four-year course of neuroleptic treatment is 16.5% (Chakos et al., *Arch. Gen. Psychiatry* 53:313,1996). The cumulative incidence is substantially higher in older people and in those being treated with neuroleptics for conditions other than schizophrenia, such as bipolar disorder (manic-depressive illness) (see, e.g., Hayashi et al., *Clin Neuropharmacol* 19:390, 1996, Jeste et al., *Arch. Gen. Psychiatry* 52:756, 1995).

TD is associated with a variable degree of cognitive impairment. Cognitive dysfunction associated with TD may involve attention, concentration, memory, or executive functions such as judgment or abstract reasoning. (see, e.g., Sachdev et al., *Acta Psychiatr Scand* 93:451, 1996; Waddington & Youssef, *Psychol Med.* 26:681, 1996; Swartz, *Neuropsychobiology* 32:115, 1995).

While the pathophysiologic mechanism of tardive dyskinesia is unknown, it has been established that chronic or prolonged administration of typical neuroleptics, all of which act by blocking dopamine receptors results in hypersensitivity or up-regulation of dopamine receptors in the basal ganglia. (see e.g., Andrews, *Can J Psych* 39:576, 1994; Casey, D. E. in *Psychopharmacology: The Fourth Generation of Progress,* Raven Press, 1995). The first major hypothesis about the pathophysiology of TD was that TD was the result of this neuronal hypersensitivity to the effects of dopamine. Drugs that increase or enhance dopamine response, especially indirect dopamine agonists, can aggravate the disorder. Many psychiatrists avoid using dopamine agonist anti-Parkinson drugs in neuroleptic therapy because of a concern that increased dopamine will aggravate tardive dyskinesia. (Bezchibnyk-Butler & Remington, *Can J. Psych.* 39:74, 1994).

Other studies have suggested that irreversible cases of tardive movement disorders may be related to excitotoxic damage to the basal ganglia (Andreasen & Jorgensen, 1994). An acquired deficiency of the inhibitory neurotransmitter GABA has also been implicated in the development of TD (Delfs et al. *Experimental Neurol.* 133:175–188, 1995).

The physical manifestations of TD can resemble movement disorders associated with degenerative diseases such as Huntington's disease and Parkinson's disease. In particular, patients with Huntington's disease may demonstrate limb movements (chorea) similar to those seen in patients with TD. In addition, the neck, trunk and limb movements of TD may resemble those caused by the "peak-dose dyskinesia" associated with prolonged levodopa treatment of Parkinson's disease.

Recent research suggests that Vitamin E can reduce symptoms of TD modestly (Lohr & Caliguiri, *J Clin Psychiatry* 57;167, 1996; Dabiri et al. 1994). GABA agonists such as baclofen and various benzodiazepines have also been the subject of some positive reports and are widely used in practice to ameliorate the symptoms of TD. (Gardos & Cole, "The Treatment of Tardive Dyskinesias", in Psychopharmacology: The Fourth Generation of Progress, eds. Bloom and Kupfer, pp. 1503–1510, 1995). This same review reports variable benefits associated with other agents including propranolol, clonidine, cholinergic agonists, buspirone and calcium-channel antagonists. However, none of these has become a generally accepted treatment for either the movement or cognitive disorders associated with TD. In co-pending, commonly-owned application Ser. No. 08/861,801, incorporated herein by reference, treatment with memantine, a congener of amantadine and a N-methyl-D-aspartate type (NMDA) receptor blocker as well as a dopamine agonist, has been suggested as an effective treatment of both the movement and cognitive disorders associated with TD.

Acamprosate (calcium N-acetylhomotaurinate) is the calcium salt of a derivative of the amino acid taurine. It is known to be an agonist at GABA receptors. Moreover, it reduces the postsynaptic response of NMDA-type glutamate receptors and reduces calcium influxes through voltage-operated channels. (Wilde & Wagstaff, *Drugs* 53:1039–53, 1997) Acamprosate is used clinically in the treatment of abstinent alcoholics to reduce or inhibit the craving for alcohol. Animal studies, reported in U.S. Pat. No. 4,355,043 issued to Durlach, showed that acamprosate had an anticonvulsant effect in one specific animal model.

An object of this invention is to develop methods for treating tardive dyskinesia using acamprosate or other homotaurine derivatives.

Another object of this invention to develop methods to treat other hyperkinetic movement disorders (i.e. tardive movement disorders) associated with prolonged exposure to neuroleptic medications or other dopamine receptor blocking agents, using acamprosate or other homotaurine derivatives with similar pharmacologic actions.

Another object of this invention is to develop methods for treating cognitive disorders, including impairments in memory associated with tardive dyskinesia and other movement disorders that are associated with prolonged exposure to neuroleptic medications.

Another object of this invention is to develop methods to treat the peak-dose dyskinesia associated with Parkinson's disease.

More particularly, it is an object of the invention to reduce the severity and duration of involuntary movements associated with tardive dyskinesia.

More particularly, it is the object of this invention to develop methods for improving cognitive function in patients exhibiting TD, specifically to increase memory, span of concentration, and everyday functional performance in activities particularly dependant upon cognition. These improvements in function are measured both subjectively and objectively. The improvement in memory can be demonstrated by standard neuropsychological tests.

Another object of the invention is to develop methods of treating or retarding the onset of tardive dyskinesia in abstinent alcohol abusers who are treated with neuroleptics for concurrent mental disorders, such as bipolar disorder and schizophrenia.

SUMMARY OF THE INVENTION

The invention relates to a method of treating tardive dyskinesia and similar movement disorders in humans. In one aspect, the invention reduces involuntary movements or hyperkinesia characteristic of patients with tardive movement disorders, including tardive dyskinesia, by the administration of a pharmacological agent such as acamprosate or other homotaurine derivative that acts as an agonist at GABA receptors and also decreases NMDA receptor function by an indirect or modulatory mechanism.

A final object of this invention is to develop a method of treating TD and related conditions by combining memantine or a similar non-competitive NMDA receptor antagonist with acamprosate or another compound or mixture that simultaneously decreases the postsynaptic response to glutamate at NMDA-type receptors and also acts a GABA agonist.

In relation to the first aspect of the invention, I have discovered that an agent used in the treatment of abstinent alcoholics, not contemplated for use in treatment of tardive dyskinesia, are effective in reducing the hyperkinesia of patients with TD. Several years ago, I hypothesized that TD represents a form of non-linear oscillation in neural circuits involving the basal ganglia, and that oscillation might be reduced by agents that block excitatory neurotransmission. Evidence from PET scans documented increased metabolism in the globus pallidus and primary motor cortex in schizophrenic patients with TD, but not in those without TD (Pahl et al., *J Neuropsych Clin Neurosci* 7:457, 1995). This suggests that TD is associated with hyperactivity in a motor control circuit, which might be part of the putative nonlinear oscillator.

As noted above, I have advanced the hypothesis that agents which act to reduce the gain in a motor control circuit through the striatum, may have a beneficial action on TD and related movement disorders. GABA is an inhibitory neurotransmitter in the striatum. Thus, support for my hypothesis comes from animal evidence that agents that directly or indirectly stimulate GABA receptors can decrease neuroleptic-induced dyskinesias (Stoessl, *Pharmacol Biochem Behav* 54:541, 1996; Gao et al. *J Neural Transmission* 95:63, 1993). Rats with neuroleptic-induced dyskinesia demonstrate decreased striatal levels of glutamic acid decarboxylase, the rate-limiting enzyme in the production of GABA (Delfs et al., *Exp Neurol* 133:175, 1995).

Without limiting the biochemical mechanism of the invention to that described here, it appears that drugs that act to reduce the gain in the hypothesized oscillator circuit would reduce the involuntary movements of tardive dyskinesia. In my co-pending patent application, Ser. No. 08/861,801, the teachings of which are incorporated herein by reference, I disclosed that certain antagonists of excitatory neurotransmitters were effective in treating both the movement and cognitive disorders associated with TD and other hyperkinetic movement disorders. In the current invention, I disclose that acamprosate, a GABA-receptor agonist that also diminishes the postsynaptic response of NMDA-type receptors to glutamate can ameliorate TD as well as related involuntary movements and cognitive symptoms. From this, and from hypothesis advanced earlier, I infer that a broad range of agents with similar concurrent action on GABA and NMDA receptors will diminish the symptoms and signs of TD and related disorders. These include derivatives of homotaurine and N-acetylhomotaurine.

In one preferred embodiment of this aspect of the invention, a pharmaceutical agent is selected from the group of agents that act as GABA-receptor agonists and also act to decrease NMDA receptor function by an indirect or modulatory mechanism such as, in a non-limiting fashion, acamprosate calcium (calcium N-acetylhomotaurinate), other salts of N-acetylhomotaurinate, acetylhomotaurine base, homotaurine or derivatives of these compounds ("Drug List A"). In another preferred embodiment, a pharmaceutical agent is selected from the group of agents that have the ability to reduce excitatory post-synaptic potentials in striatal cells induced by glutamate, such as, in a non-limiting fashion, acamprosate calcium, calcium acetyl homotaurinate, homotaurine or derivatives of these compounds. In another preferred embodiment, a combination of two or more pharmaceutical agents is selected such that the combination acts concurrently to stimulate GABA-receptors and to attenuate the response of NMDA-type glutamate receptors. A third embodiment is to combine such a compound or mixture with memantine or a similar non-competitive NMDA-receptor blocking agent.

A second aspect of the invention features a method of improving cognitive memory and cognition in humans with TD, where the latter is demonstrated by performance on neuropsychological tests, including without limitation, the Rey Auditory-Verbal Learning Test, and measurement of Choice Reaction Time, and by subjective indicators of performance at tasks highly dependent on cognitive processes. It will be obvious to one skilled in the art that numerous different neuropsychological tests could be employed to demonstrate that cognitive function improved in patients on a treatment regime that included acamprosate.

DETAILED DESCRIPTION OF PREFERRED EMBODIMENTS

GABA-receptor agonists can be used according to the method of the invention to reduce the severity of hyperkinesia associated with tardive dyskinesia. However, such agents have not been shown to mitigate the severity of the cognitive dysfunction associated with TD.

Generally, the method of the invention can be used for the treatment of tardive dyskinesia, including the treatment of the hyperkinesia, cognitive disorders and excitotoxic-related neurological damage associated with the disorder.

The method relates to the administration of an effective dose of a GABA-receptor agonist chosen from among a group of GABA-receptor agonists that also modulate NMDA-type glutamate receptors so as to decrease their response, which include, in a non-limiting fashion, acamprosate calcium (calcium N-acetylhomotaurinate) other salts of N-acetylhomotaurinate, acetylhomotaurinate base, homotaurine or derivatives of these compounds.

Acamprosate is a GABA-receptor agonist that resembles the inhibitory neurotransmitter GABA. Acamprosate also reduces the post-synaptic response of NMDA-type glutamate receptors and reduces calcium influxes through voltage-operated channels.

In the method of the claimed invention, "acamprosate" refers to acamprosate calcium (calcium N-acetylhomotaurinate) other salts of N-acetylhomotaurinate, acetylhomotaurinate base, homotaurine or derivatives of these compounds.

In the method of the claimed invention, "GABA-receptor agonist" refers to molecules that are capable of binding to active or modulatory sites on the GABA receptor.

In the method of the claimed invention, "effective" dose refers to one that is administered in doses tailored to each individual patient manifesting symptoms of tardive dyskinesia sufficient to cause a reduction in the associated hyperkinesia or an improvement in the associated cognitive disorders with tolerable adverse effects. Experimentally, doses of acamprosate ranging from 333 mg. to 666 mg. administered three to four times daily have been shown to be effective, but a person skilled in the art will recognize that treatment of patients with pharmaceutical agents must be tailored to the individual patient, taking into account the patient's height, weight, rate of absorption and metabolism of the medication in question, and stage of the disorder to be treated, as well as what other pharmacological agents are administered concurrently, if any.

The following case reports illustrate the preferred method of the invention:

Case Report 1

A 45-year old woman had long-standing TD, originally induced by seven years exposure to amoxapine, an antidepressant drug with neuroleptic effects. The patient's irregularly-rhythmic movements consisted of forced eye blinking (blepharospasm), thrusting of the tongue forward and from side to side, tongue twisting, grimacing, shoulder shrugging, and tensing of the platysma muscles of the neck. The patient is a semi-professional musician; the dyskinetic movements were accompanied by significant occupational disability, including difficulty reading music or text and difficulty playing woodwind instruments. She had impaired attention, concentration and memory compared with her performance before onset of TD. She had significant fatigue, and usually required rest at some point during each day. The patient was diagnosed with TD by a board-certified neurologist with extensive experience in evaluating neuroleptic-induced side effects.

Hyperkinesia worsened after the amoxapine was discontinued. Palliative treatment with alprazolam (an anxiolytic and GABA agonist via modulation; dosage 0.25 mg four times a day) and trihexyphenidyl (an anticholinergic antiparkinson drug that inhibits dopamine re-uptake at synapses; dosage 2 mg twice a day) was prescribed by another physician. This combination produce minimal improvement. The patient began treatment with me in the winter of 1992 and was maintained on trihexyphenidyl for an additional 18 months. Trihexyphenidyl was then discontinued without a change in her involuntary movements. During 1993, alprazolam was increased to 0.5 mg four times a day, to treat mild symptoms of anxiety; the change in dosage had no detectable effect on the patient's involuntary movements.

Treatment trials with buspirone, sertraline, verapamil, and vitamin E in 1992 either produced little benefit or were not tolerated at doses that slightly reduced her involuntary movements. None of these drugs significantly improved the patient's everyday function, i.e., her performance at reading text or music, her stamina or her ability to concentrate. The first drug that provided significant and sustained benefits was nimodipine, a cerebroselective calcium channel blocker, which, beginning in 1993, was administered in a regime that included 30 mg of nimodipine four times a day. This regime reduced the patient's hyperkinesia by about 50% but she experienced adverse effects, including dizziness, lightheadedness, and palpitations and had no symptomatic improvement in cognitive function. There was a meaningful improvement in her ability to read and to play music. However, even with this improvement, she could read text or music for no more than 30 minutes at a time, before fatigue or blepharospasm prevented her continuing.

In 1995, memantine came to my attention as a relatively non-toxic NMDA receptor antagonist. In view of my hypothesis about the pathophysiology of tardive dyskinesia, I thought that memantine might be beneficial in its treatment. Nimodipine was discontinued, and the patient was begun on memantine at a dosage of 10 mg twice a day. The hyperkinetic movements with TD were reduced within 24 hours of administration of memantine, to a substantially greater degree than had been observed with nimodipine. Adverse effects included a sense of mild intoxication. Adjustments to the therapeutic regime were made such that the drug was reduced to 5 mg three times a day, with the result that the therapeutic benefits were maintained without perceptible side effects. In addition, the patient reported improved energy, attention, and concentration.

Prior to treatment with acamprosate, the patient's involuntary movements (on an optimal dose of memantine) consisted of eye blinking, puckering of the cheeks, writhing of the tongue and tensing of the platysma. These involuntary movements were usually mild and occasionally moderate in intensity. The movements had been substantially more severe in the past, but had been reduced significantly during the course of two-year course of treatment with memantine, an NMDA-type glutamate receptor antagonist. Moreover, the patient's involuntary movements were accompanied by mild but definite cognitive impairment. The patient's most prominent cognitive symptom was difficulty sustaining concentration long enough to read more than a few pages of text.

The patient was taken off of memantine and treated with acamprosate, using a treatment regime of 333 mg. acamprosate given four times a day. On acamprosate, the patient's involuntary movements became imperceptible.

In addition, the patient's cognitive function improved significantly when measured both subjectively and objectively. For example, the patient was able to sustain concentration for prolonged periods while on acamprosate, including the ability to read a book for over an hour at a time, with good recall of what she had read. The patient's cognitive improvement was also assessed using formal neuropsychological measures. The patient was tested while on the drug, then taken off of the drug and tested two days later. On the drug, the patient was able to recall 13 of the 15 items after a short delay as well as 13 of the 15 items after a long delay, as measured by the Rey Auditory Verbal Learning Test. This was in comparison to the patient's ability while off the drug to recall only 7 of the 15 items after a short delay as well as 8 of the items after a long delay in tests performed. In addition, the patient was able to recognize all 15 of the items while on acamprosate but while off the drug (and while having been off of memantine for over 2 months) the patient could only recognize 10 of the items.

Comparison with other neuropsychological tests demonstrated that the improved cognitive findings shown while the patient was on acamprosate were not explained by a non-specific lack of effort or to concentration during the period that the patient was not on the acamprosate regime. These additional tests, which reflect basic attention and psychomotor speed, showed that the patient had slightly better results off acamprosate for attention and concentration. The tests showing such results included Simple Reaction Time, the Trail Making Test (both parts) and the Paced Auditory Serial Addition Test (PASAT). Choice reaction time, a test requiring both basic attention and concentration on a specific task that must be kept in mind, was slightly better on acamprosate, consistent with the hypothesis that general cognitive function, as opposed to simple attention, improves with acamprosate treatment. In addition, normal results were shown while on and while off acamprosate during a vigilance test.

The following tables report on the results of these neuropharmalogical tests (Drug I is memantine and Drug II is acamprosate):

TABLE 1

REACTION TIME, PSYCHOMOTOR SPEED, & MOTOR FUNCTIONING FOR DRUG I (MEMANTINE) AND DRUG II (ACAMPROSATE)

| TESTS | 2/23/94 | 2/23/96 ON DRUG I | 4/8/96 OFF DRUG I | 9/23/97 ON DRUG II | 9/25/97 OFF DRUG II |
|---|---|---|---|---|---|
| Simple Reaction Time[a] | | | | | |
| 1500 Green | NA | 212 msec | 332 msec | 261 msec | 234 msec |
| 1500 Red | NA | 224 msec | 276 msec | 264 msec | 241 msec |
| 500 Green | NA | 284 msec | 343 msec | 286 msec | 272 msec |
| 500 Red | NA | 266 msec | 382 msec | 272 msec | 237 msec |
| Choice Reaction Time[a] | | | | | |
| 1500 Green | NA | 365 msec | 542 msec | 408 msec | 442 msec |
| 1500 Red | NA | 422 msec | 643 msec | 379 msec | 435 msec |
| 500 Green | NA | 362 msec | 603 msec | 382 msec | 425 msec |
| 500 Red | NA | 421 msec | 557 msec | 426 msec | 413 msec |
| PASAT[a] | | | | | |
| 2.4 sec ISI errors | 17/49 | 13/49 | 15/49 | 4/49 | 0/49 |
| 2.0 sec ISI errors | 17/49 | 17/49 | 21/49 | 1/49 | 1/49 |
| 1.6 sec ISI errors | 11/49 | 21/49 | 22/49 | 11/49 | 4/49 |
| 1.2 sec ISI errors | 17/49 | 28/49 | 25/49 | 13/49 | 11/49 |
| Digit Symbol[b] | NA | 34 | 20 | NA | NA |
| Trails A | | | | | |
| Seconds[a] | 25" | 28" | NA | 20" | 16" |
| Errors[a] | 1 | 0 | NA | 0 | 0 |
| Motor Functions | | | | | |
| Grooved Functions sec.[a] DH = right | DH = 68" NDH = 82" | DH = 71" NDH = 70" | NA | DH = 61" NDH = 70" | DH = 59" NDH = 76" |
| Finger Tapping[b] | DH = 58.8 NDH = 41.6 | DH = 59.3 NDH = 48.5 | NA | NA | NA |
| Grip Strength[b] | NA | DH = 17.7 NDH = 21.7 | NA | NA | NA |

Note:
[a] lower score indicative of better performance
[b] higher score indicative of better performance

TABLE 2

EXECUTIVE, ATTENTION, VISUOCONSTRUCTIONAL & VISUAL MEMORY TASKS FOR DRUG I (MEMANTINE) AND DRUG II (ACAMPROSATE)

| TESTS | 2/23/94 | 2/23/96 ON DRUG I | 4/8/96 OFF DRUG I | 9/23/97 ON DRUG II | 9/25/97 OFF DRUG II |
|---|---|---|---|---|---|
| 1. Trails B | | | | | |
| Seconds[a] | 56" | 118" | NA | 43" | 39" |
| Errors[ab] | 0 | 0 | NA | 0 | 0 |
| Verbal Fluency | | | | | |
| Letter (CFL)[b] | NA | Total = 70 Per = 2[b] | NA | NA | NA |
| Category (Animals)[b] | NA | Total = 25 Per = 0[b] | NA | NA | NA |
| Figural Fluency | | | | | |
| Unique Designs[b] | NA | 124 | 99 | NA | NA |
| Perservations[a] | NA | 8 | 4 | NA | NA |
| 2. CPT - with conditions (Vigilance) | | | | | |
| Commission errors[a] | 0 | NA | NA | 0 | 0 |
| Omission errors[a] | 0 | NA | NA | 0 | 0 |
| wrong[a] | 3 | NA | NA | 3 | 0 |
| Correct[b] | 50/50 | NA | NA | 100/100 | 100/100 |

TABLE 2-continued

EXECUTIVE, ATTENTION, VISUOCONSTRUCTIONAL &
VISUAL MEMORY TASKS FOR DRUG I (MEMANTINE) AND
DRUG II (ACAMPROSATE)

| TESTS | 2/23/94 | 2/23/96 ON DRUG I | 4/8/96 OFF DRUG I | 9/23/97 ON DRUG II | 9/25/97 OFF DRUG II |
|---|---|---|---|---|---|
| 3. Rey-Osterrieth Complex Figure | | | | | |
| Copy Presence & Accuracy[b] | NA | 20 | 17 | NA | NA |
| Copy Organization[b] | NA | 5 | 4 | NA | NA |
| Immediate Retention[b] | NA | −55 | −47.1 | NA | NA |
| Delayed Retention[b] | NA | −11.1 | 22.2 | NA | NA |

Note:
[a]lower score indicative of better performance
[b]higher score indicative of better performance

TABLE 3

MEMORY TESTING FOR DRUG I (MEMANTINE) AND DRUG
II (ACAMPROSATE)

| TESTS | 2/23/94 | 2/23/96 ON DRUG I | 4/8/96 OFF DRUG I | 9/23/97 ON DRUG II | 9/25/97 OFF DRUG II |
|---|---|---|---|---|---|
| California Verbal Learning Test 16-items | | | | | |
| List A 1-5 total (80 max)[b] | NA | 53 | 40 | NA | NA |
| List A Trial 1[b] | NA | 7 | 6 | NA | NA |
| List A Trial 5[b] | NA | 13 | 9 | NA | NA |
| List B[b] | NA | 7 | 5 | NA | NA |
| Short-Delay Free Recall[b] | NA | 10 | 4 | NA | NA |
| Short-Delay Cued Recall[b] | NA | 13 | 9 | NA | NA |
| Long-Delay Free Recall[b] | NA | 12 | 7 | NA | NA |
| Long-Delay Cued Recall[b] | NA | 15 | 8 | NA | NA |
| Perseverations[a] | NA | 23 | 4 | NA | NA |
| Intrusions[a] | NA | 6 | 0 | NA | NA |
| Recognition Hits[b] | NA | 16 | 14 | NA | NA |
| False Positives[a] | NA | 3 | 0 | NA | NA |
| Rey-Auditory Verbal Learning Test 15-items | | | | | |
| List A 1-5 toal (75 max)[b] | NA | NA | NA | 63 | 57 |
| List A Trial 1[b] | NA | NA | NA | 10 | 9 |
| Ljst A Trial 5[b] | NA | NA | NA | 14 | 14 |
| List B[b] | NA | NA | NA | 8 | 9 |
| Short-Delay Free Recall[b] | NA | NA | NA | 13 | 7 |
| Long-Delay Free Recall[b] | NA | NA | NA | 13 | 8 |
| Perseverations[a] | NA | NA | NA | 5 | 0 |
| Intrusions[a] | NA | NA | NA | 0 | 3 |

TABLE 3-continued

MEMORY TESTING FOR DRUG I (MEMANTINE) AND DRUG
II (ACAMPROSATE)

| TESTS | 2/23/94 | 2/23/96 ON DRUG I | 4/8/96 OFF DRUG I | 9/23/97 ON DRUG II | 9/25/97 OFF DRUG II |
|---|---|---|---|---|---|
| Recognition Hits[b] | NA | NA | NA | 15 | 10 |
| False Positive[a] | NA | NA | NA | 1 | 2 |

Note:
[a]lower score indicative of better performance
[b]higher score indicative of better performance In addition to a markedly reduced degree of involuntary movements and meaningfully increased cognitive ability experienced by the patient while on the acamprosate regime, the patent also experienced an increase in stamina. Prior to beginning the acamprosate regime, the patient was fatigued by the end of the afternoon, requiring rest in order to be alert in the evening. This fatigue was significantly less while on the acamprosate regime, with a corresponding decline in fatigue-related cognitive function. On acamprosate, the patient no longer needed to rest during the day in order to be alert and active during the evening.

To verify that the acamprosate was related to the patient's improvement in controlling movement disorders, cognitive function and stamina, the patient was removed from the acamprosate regime (as well as the memantine regime) for a period of four weeks. During the initial two-week period off acamprosate, the patient's involuntary movements gradually returned to her pre-acamprosate, off-memantine baseline. (While the patient's off-drug baseline was less severe than it was when she started on memantine two years earlier, her movements still were severe enough to interfere significantly with her everyday functioning.) From that point on, until acamprosate was re-instituted, she showed continual mild-to-moderate grimacing, tensing of the platysma, and forced eye closure. These involuntary movements worsened still further during periods of stress or fatigue. Moreover, the patient fatigued much more easily, to a degree that noticeably reduced her everyday functioning. Subjectively, the patient reported that concentration and memory both decreased.

Within two days of re-instituting treatment with acamprosate, the patient reported that her energy, stamina, concentration and memory improved to the level experienced during her prior treatment with acamprosate. In addition, the patient's involuntary movements were absent except for very mild movements during times of stress.

Case Report 2

A 79-year old woman had long-standing TD following decades of treatment with the neuroleptic drug perphenazine. Her involuntary movements comprised bilateral chorea of the upper extremities, plus writhing of the tongue and tongue-biting. Both of the latter movements led to a very sore tongue. In addition, the patient experienced impairment of her short-term memory, which was attributed primarily to cerebrovascular disease.

Following treatment with memantine the patient's voluntary movements improved, but continued at a mild-to-moderate level. She also continued to have a sore tongue. Her cognitive symptoms did not improve. In addition to memantine, the patient regularly took antiepileptic drugs (gabapentin and lamotrigine), antiplatlet agents (aspirin and ticlopidine) as well as medications for hypertension, glaucoma and gastrointestinal symptoms (isosorbide mononitrate, metoprolol, timolol eye drops and olsalazine). These various drugs did not affect the patient's involuntary movements or cognitive symptoms; there was no noticeable change in either one at the time that each of the above-mentioned drugs was instituted.

The patient was placed on a treatment regime that included administration of 666 mg. of acamprosate, three times daily. In this case, acamprosate was added to the patient's regimen, which continued to include memantine. Once the patient began taking acamprosate, her chorea and tongue-biting stopped completely, and the writhing movements of the tongue diminished substantially. Subjectively, the patient's memory improved to the extent that her long-term bridge partner stated that that patient was noticeably better at remembering cards during the play of duplicate bridge. Despite past evidence from formal testing that the patient had impaired short-term memory, she performed normally on a two-sentence memory task, which involved testing the patient's recall ability using two sentences containing 13 separate details. Under the two-sentence memory task, within three attempts the patient was able to recall 9 details and, using a multiple choice format, was able to recall a total of 11 details.

Case Report 3

A 56-year old female professor of nursing had had Parkinson's disease since her late 30s. The patient's Parkinson's disease was treated using levodopa/carbidopa and bromocriptine. The patient's profession required a high level of mobility and physical effort, but taking a sufficient dosage of the levodopa/carbidopa to allow adequate physical functioning at work resulted in the patient demonstrating severe peak-dose dyskinesia. The patient's manifestations of peak-dose dyskinesia consisted of writhing movements of the upper trunk, jerky lateral and rotatory movements of the neck as well as chorea of both upper extremities. The patient accepted these involuntary movements because lower dosages of levodopa-carbidopa left her too rigid and hypokinetic to perform her job.

Prior to beginning treatment with acamprosate, the patient was on an antiparkinson treatment regime that consisted of 1 mg. of pergolide administered three times a day, 5 mg. of selegiline administered twice a day, and a combination of levodopa/carbidopa consisting of 550–600 mg. of levodopa and 125–150 mg. of carbidopa administered in divided doses. Additional medications that did not appear to affect her parkinsonism or dyskinesia consisted of bethanecol, sertraline, conjugated estrogens and medroxyprogesterone. (As with the additional medications mentioned in Case 2, there had been no noticeable change in the patient's parkinsonism or dyskinesia after the introduction of each of the drugs listed.) The patient also received 10 mg. of memantine three times a day, which had previously reduced her dyskinetic movements from severe to mild-to-moderate.

The patient began acamprosate as an addition to the antiparkinson regime described above. Initially, the patient received 666 mg. of acamprosate administered three time a day. Two weeks later the regime was adjusted such that the patient received 333 mg. of acamprosate administered four times a day, taking one 333 mg. pill with each dose of 100 mg. levodopa and 25 mg. carbidopa. The patient's bedtime does of controlled-release levodopa-carbidopa (200 mg. of levodopa and 50 mg. of carbidopa) was continued, but given without acamprosate. As soon as acamprosate was added to her regimen, the patient's severe peak-dose dyskinesia was reduced to from moderate to mild intensity, and there were periods of up to two hours following each dose during which there was no dyskinesia at all. There was no decrease in the efficacy of the levodopa/carbidopa treatment of her hypokinesia and rigidity. On acamprosate, the patient experienced longer periods where she was able to exhibit good motor function, and she now had no periods at all where her motor function was inadequate for work or social activity. The reduction of the dyskinesia to a minimal level led to a substantial improvement in purposeful motor function of the upper extremities. Thus, the patient's overall motor function was significantly improved, compared with the treatment regime that did not include acamprosate.

To confirm that the patient's improvement was due to the administration of acamprosate, the patient was taken off the acamprosate, which was replaced first with a daily dose of 30 baclofen (a GABA-receptor agonist) at a total daily dose of 30 mg, and then with baclofen at a total daily dose of 60 mg. These doses of baclofen were high enough to produce sedation and nausea, but they had no beneficial effect on the patient's dyskinesia. Within one day of stopping acamprosate, the patient's dyskinetic movements were as severe as they had been before acamprosate was first given. . . . Upon reinstituting acamprosate, the patient experienced an immediate reduction in her dyskinetic movements. Additional improvement was obtained by replacing the pergolide with 1 mg. of pramipexole administered three or four times a day.

Discussion

The three patients discussed above all exhibited a marked decrease in the incidence and severity of dyskinetic movements. Those patients who previously exhibited cognitive disorders showed functionally significant improvement in cognitive function after beginning treatment with acamprosate. This evidence supports my novel hypothesis that acamprosate, or a derivative with similar pharmacodynamic actions, will be helpful in the treatment of hyperkinetic movement disorders and associated cognitive disorders. Acamprosate and similar drugs have an action on GABA receptors and effect on the function of NMDA-type glutamate receptors that may be synergistic in regards to the therapy of hyperkinetic movement disorders. To the extent that other related compounds and mixtures of compounds also simultaneously affect GABA and NMDA-type glutamate systems, these related compounds may have the same or similar action on movement disorders or their associated cognitive impairments. Related compounds include, but are not limited to acamprosate calcium (calcium N-acetylhomotaurinate) other salts of N-acetylhomotaurinate, acetylhomotaurinate base, homotaurine or derivatives of these compounds. Derivitives of acamprosate also specifically include those produced by substituting alkyl (e.g. methyl) or aromatic (e.g. benzyl) groups for either or both of the hydrogens in N-acetylhomotaurine. Either those compounds or their salts are included.

Acamprosate may have benefits for treating hyperkinetic movement disorders other that TD. Case 3 suggests that acamprosate was effective in treating a patient with the peak-dose dyskinesia of treated Parkinson's disease. It will be obvious to someone skilled in the art that acamprosate may also benefit patients with hyperkinetic movement disorders with symptoms and/or pathophysiology similar to that of TD or of peak-dose dyskinesia. The movement disorder associated with Huntington's disease is an example.

Patients with Huntington's disease may show dyskinetic movements of the face and limbs resembling those of TD. Patients with Huntington's disease have a deficiency of GAD in the striatum, and are thought to suffer from neuronal death due to NMDA-receptor mediated excitotoxicity (D E Riley and A E Lang: Movement Disorders, in W G Bradley et al., editors, Neurology in Clinical Practice, Boston: Butterworth-Heinemann, 1991, p. 1568). These features of the disorder favor a positive response to acamprosate, a drug with joint actions on GAD and NMDA-receptors.

One aspect of the method of the invention features improvements in the cognitive disorder associated with TD. The improvement in cognition and everyday functional performance seen during the treatment of TD, makes acamprosate particularly attractive for patients with cognitive impairment that frequently accompanies TD.

The relationship between tardive dyskinesia and cognitive impairment is not fully understood. It is known that pre-existing cognitive impairment increases the risk that TD will develop in the event a patient receives neuroleptics over a long-term period. It is also known that treated schizophrenics with TD are more likely to show progressive cognitive deterioration that those without TD. However, it is not known whether treatment of TD will ameliorate the cognitive deficits associated with TD. Cases 1 and 2 discussed above suggest that indeed treatment of TD will ameliorate such cognitive deficits given that the prior art does not report that the administration of acamprosate when used as a treatment for alcoholism improves cognitive deficits. Because the prior art does not report that the administration of acamprosate when used as a treatment for alcoholism improved the patients' cognition, it is reasonable to infer that the improvement in cognition seen in Cases 1 and 2 was related to the improvement in their movement disorders. This is consistent with the well-established involvement of the basal ganglia in cognitive processes (Sano et al., Basal Ganglia Diseases)

Moreover, the fact that acamprosate is also known as an agent used in the treatment of alcoholism makes acamprosate particularly suited for the treatment of patients who have a history of alcoholism in addition to a hyperkinetic movement disorder.

Additional tests of the effectiveness of acamprosate are planned, contingent on obtaining an IND permit from the US FDA. Dr. Dilip Jeste of the University of California at San Diego, a world authority on TD, has designed a protocol for an open-label study of 20 patients with severe to extremely-severe TD. The study calls for such patients to be studied over a 12-week period, with objective measures of both involuntary movements and cognition.

Based on the foregoing, what I claim is the following:

1. A method of treating hyperkinesia comprising:
   administering an effective and non-toxic dose of an agent which is a GABA-receptor agonist and which decreases the response of NMDA-type glutamate receptors.

2. The method of of claim 1 wherein said agent is selected from the group consisting of acamprosate, calcium N-acetylhomotaurinate, salts of N-acetylhomotaurinate, acetylhomotaurinate base, homotaurine and derivatives thereof.

3. The method of claim 2 whereby said method of treating hyperkinesia also improves cognition or memory in humans exhibiting signs of tardive dyskinesia when said response is determined using a standard neuropsychological test.

4. The method of claim 3 wherein said standard neuropsychological test is selected from the group consisting of established clinical tests, established bedside tests of cognition or memory, and observation of a history of performance of everyday activities that are highly dependant on cognitive processes.

5. The method of claim 1 wherein said step of administering comprising oral administration.

6. A method of treating a hyperkinetic movement disorder comprising the steps of:
   selecting a first at least one pharmacologically active agent that acts as a GABA-receptor agonist and a second at least one pharmacologically active agent that acts as a NMDA-type glutamate receptor antagonist; and
   administering said first and said second agents at effective and non-toxic dosages.

7. The methods of claim 6 whereby said first agent and said second agent are the same agent.

8. The method of claim 6 whereby said movement disorder is tardive dyskinesia or comprises involuntary movements similar to those seen in said tardive dyskinesia.

9. The method of claim 6 whereby said movement disorder is the peak-dose dyskinesia associated with Parkinson's disease or comprises involuntary movements similar to those seen in said peak-dose dyskinesia.

10. The method of claim 6 whereby said movement disorder is associated with Huntington's disease.

11. The method of claim 6 whereby said method further improves cognitive response in humans exhibiting said movement disorder when said response is measured using standard neuropsychological tests.

12. The method of claim 11 wherein said standard neuropsychological test comprises established clinical tests, established bedside tests of cognition and memory, and observation of a history of clear-cut changes in performance of everyday activities highly dependant on cognitive processes.

13. The method of claim 6 wherein said movement disorder is related to a deficiency in GABA in the basal ganglia.

14. The method of claim 6 wherein said movement disorder is related to NMDA-based excitotoxicity.

15. The method of claim 6 comprising the further steps of
   selecting a third pharmacologically active agent that is a noncompetitive antagonist at NMDA receptors; and
   administering said third agent in conjunction with said first and said second agents.

16. The method of claim 15 wherein said third agent is memantine or a derivative thereof.

* * * * *